United States Patent
Salomonson et al.

(10) Patent No.: US 7,600,398 B2
(45) Date of Patent: Oct. 13, 2009

(54) METHOD FOR MAKING CERAMIC ARTIFICIAL DENTAL BRIDGES

(75) Inventors: Jonas Salomonson, Huddinge (SE); Joseph Yanez, Washington, DC (US)

(73) Assignee: Nobel Biocare AB, Göteborg (SE)

( * ) Notice: Subject to any disclaimer, the term of this patent is extended or adjusted under 35 U.S.C. 154(b) by 0 days.

(21) Appl. No.: 10/500,003

(22) PCT Filed: Dec. 23, 2002

(86) PCT No.: PCT/SE02/02440

§ 371 (c)(1), (2), (4) Date: Jun. 24, 2005

(87) PCT Pub. No.: WO03/055408

PCT Pub. Date: Jul. 10, 2003

(65) Prior Publication Data

US 2006/0174653 A1 Aug. 10, 2006

(30) Foreign Application Priority Data

Jan. 3, 2002 (SE) .................................. 0200007

(51) Int. Cl.
*C03C 27/02* (2006.01)
*A61C 13/00* (2006.01)

(52) U.S. Cl. ........................ 65/59.21; 433/223; 433/218; 433/213; 433/202.1; 433/222.1; 264/16; 264/18; 156/182; 156/283; 156/325

(58) Field of Classification Search ................... 264/16; 65/36
See application file for complete search history.

(56) References Cited

U.S. PATENT DOCUMENTS

| 4,574,063 | A | * | 3/1986 | Scherer | ................. 65/395 |
| 4,772,436 | A | * | 9/1988 | Tyszblat | ................. 264/19 |
| 4,892,846 | A | * | 1/1990 | Rogers et al. | .............. 501/8 |
| 5,080,589 | A | | 1/1992 | Oden et al. | |
| 5,342,201 | A | | 8/1994 | Oden | |

FOREIGN PATENT DOCUMENTS

| WO | WO 9913795 A | 3/1999 |
| WO | WO 0170128 A | 9/2001 |

\* cited by examiner

*Primary Examiner*—Philip C Tucker
*Assistant Examiner*—Phu H Nguyen
(74) *Attorney, Agent, or Firm*—Venable LLP; Eric J. Franklin

(57) ABSTRACT

A method for making artificial tooth bridges including a ceramic densely sintered high strength individual core veneered with porcelain using powder metallurgical methods. The individual densely sintered bridge parts are joined together to a bridge core by a particle reinforced glass. Since only the glass material wets the surface of the densely sintered parts, the glass is the binding material that holds the core together and the particles function to only increase the strength of the bulk glass material.

10 Claims, 2 Drawing Sheets

METHOD FOR MAKING CERAMIC ARTIFICIAL DENTAL BRIDGES

CROSS-REFERENCE TO RELATED APPLICATIONS

This application claims priority to Swedish patent application 0200007-3 filed 3 Jan. 2002 and is the national phase under 35 U.S.C. 371 of PCT/SE02/02440 filed 23 Dec. 2002.

FIELD OF THE INVENTION

The present invention relates to a method for making artificial dental bridges accurate to shape in high strength ceramic materials, by joining of two or more ceramic parts to each other. The ceramic parts for such a joining could be manufactured using a technique as described in U.S. Pat. No. 5,342,201.

SUMMARY OF THE INVENTION

The object of the present invention is to achieve a rational manufacturing technique for dental bridges in densely sintered high strength ceramic material using modern powder metallurgical technique, registering technique, and joining technique. Dental bridges in i.e. densely sintered high strength alumina offer a combination of mechanical strength and esthetics, which is not possible with established dental materials and methods, intended for dental bridges.

The present invention relates to a method of manufacturing artificial dental bridges in densely sintered ceramic material by joining two or more densely sintered ceramic parts with the aid of a particle reinforced glass in a ONE step heating process. The individual parts, whose inner surface which should fit against one or more prepared tooth surfaces or artificial abutments, are made by forming a ceramic powder mixture against a surface of a body whereby said surface is made using a three-dimensional optical or mechanical reading method in which the surfaces of the prepared teeth or artificial abutments and their mutual relationship are registered, either directly in the mouth or on a model in e.g. plaster whereafter the registered surfaces are reproduced in an enlarged format e.g. with the aid of a computer controlled milling machine whereby the magnification is calculated considering the shrinkage of the ceramic material during sintering to full density with addition of desired gap required for cement according to U.S. Pat. No. 5,342,201 and U.S. Pat. No. 5,080,589.

DETAILED DESCRIPTION OF EMBODIMENTS OF THE INVENTION

Figure 1:
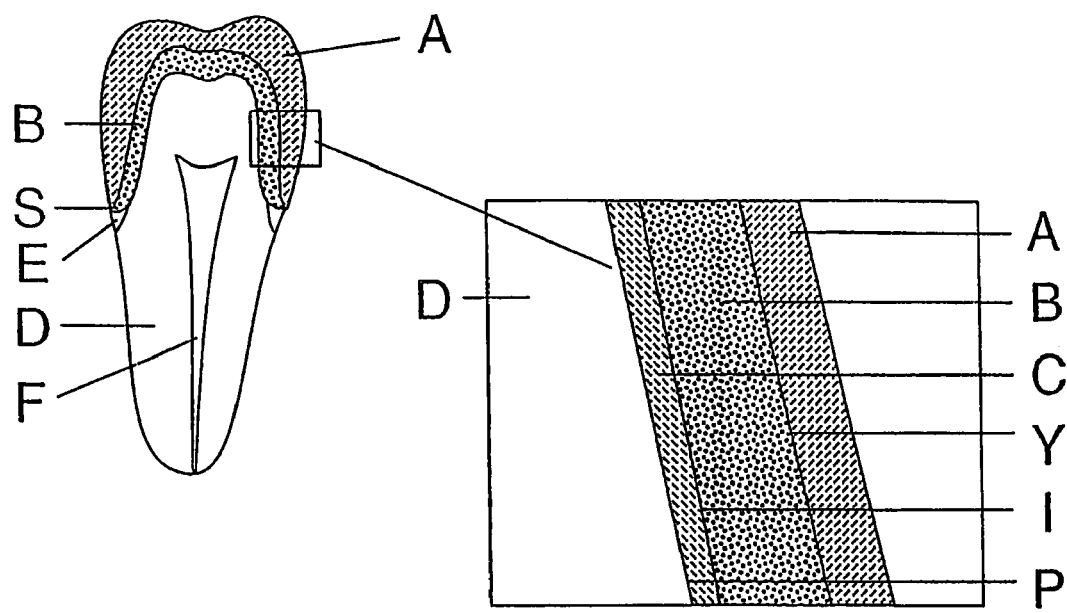
FIG. 1 shows a cross section of a natural tooth with an artificial tooth crown. In this figure, A=dental porcelain, B=core, Y=outer surface of the core, I=inner surface of the core, C=cement, P=prepared surface of the tooth, S=preparation border, E=enamel, D=dentin and F=pulp.
Figure 2:
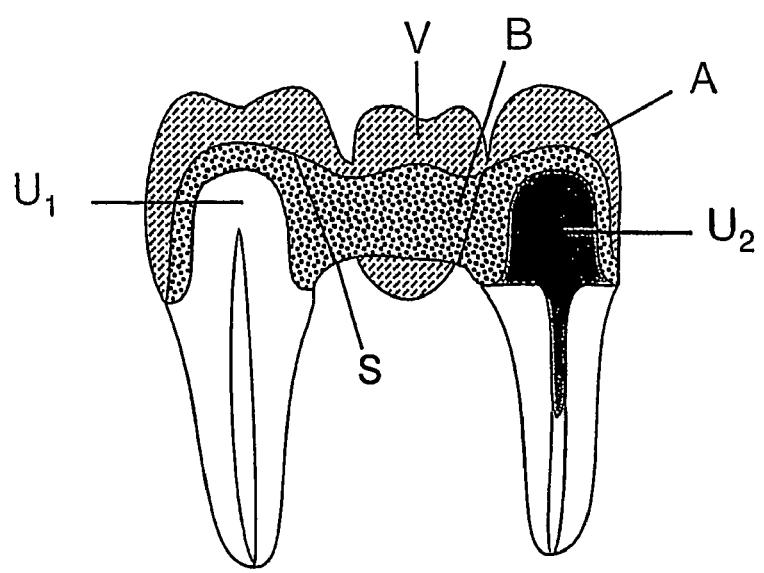
FIG. 2 shows a cross-section of a bridge containing three joined parts.

The bridge is cemented on two supporting teeth. These supporting teeth may have a vital abutment (U1) or an artificial abutment (U2) manufactured in some dental alloy, ceramic material or some reinforced polymer. The bridge contains two artificial tooth crowns according to FIG. 1 and with a central pontic (V), as a substitute for a lost tooth. The joining of the parts is accomplished in the following manner:
1) A premixed suspension of particles, dispersant for the particles, binder for the particles, and solvent (e.g. water) is applied between the parts and allowed to dry.
2) A suspension of glass material and solvent (e.g. water) is then applied to the newly formed joint of particles.
3) The bridge is then heated to a sufficient temperature and for a sufficient time so that the glass material melts and penetrated completely through the joint.

The glass material fully wets the surface of the densely sintered parts forcing the particles away from the surface. The glass will also wet the surface of each of the individual particles such that the final joint will be pure glass on the surface of the densely sintered parts and a particle reinforced glass (i.e. non-touching particles) a short distance away from the surface. Since no particles are in contact with the surface of the densely sintered parts the material binding the parts together is the glass and the particles act to only increase the strength of the glass material.

The present invention offers two significant advantages over the invention disclosed in WO 99/13795 in which only glass is used to create a joint between the various bridge parts. The first is that prior to heat treatment the dried particle network gives sufficient strength to the bridge so that it can be easily transported to a heating device without the need of a support structure and the second is that the particle reinforced glass has a higher resistance to cracking (i.e. higher $K_c$) than the pure glass material.

WO 01/70128 describes a TWO step process for connecting densely sintered parts. Similar to the present invention, the first step of WO 01/70128 calls for a premixed suspension of particles, dispersant for the particles, binder for the particles, and solvent (e.g. water) to be applied between the three parts and allowed to dry. The bridge is then transported to a heating device and the temperature is increased to a sufficient value such that a lightly sintered (i.e. porous network) is created. The bridge is then brought down to room temperature and glass applied to the joints and then heated to a sufficient temperature and for a sufficient time so that the glass material melts and penetrated completely through the joint. WO 01/70128 describes the final bridge as bound together by the lightly sintered (i.e. touching) particle network. Hence, the loosely sintered particle network is in contact with the surfaces of the densely sintered parts and acts as the binding agent. The glass material is used to fill the voids within the porous network and add addition reinforcement. The present invention has an advantage over WO/70128 A1 in that it involves a ONE step heating process, which saves both time and energy for the user.

The properties of the glass material should be such that it wets the densely sintered ceramic material i.e. the glass should have a lower surface energy at the temperature used during the joining process than the ceramic material in the bridge units. This ensures that the melted glass will easily spread out over the surfaces of the bridge units in order to lower their surface energy. The melted glass must have a low viscosity in order to be able to spread into in the gap between the bridge units. Furthermore, the glass should have the characteristic property that it reacts, not too little and not too much, with the ceramic material in the bridge units in order to get an optimal bond between glass and ceramic material in the joint. In order to obtain this the glass should contain the same metal oxides as the material in the densely sintered bridge parts. This amount should be less than saturation level of the mentioned metal oxides in the glass at the joining temperature. Its thermal expansion coefficient must be lower than or equal to the ceramic material in the bridge units in order to avoid development of fractures during cooling. The joint should be designed so that a certain mechanical locking is obtained in the direction of the main force in order to obtain an optimal strength. If the joining process of the bridge units is made with a correct refractory replica of the base model, a correctly shaped joint and with a glass with properties according to above the joined bridge becomes very strong in compression at the same time as the fit can be optimal. An example of important main constituents in a glass composition that works well when joining highly pure alumina is: $SiO_2$ 32 mol %, $B_2O_3$ 24 mol %, $Al_2O_3$ 18 mol % as well as $La_2O_3$ 12 mol %. On a bridge joined with particle reinforced glass, subsequently one or more layers of dental porcelain can be burned in order to obtain good esthetics. The advantage with manufacturing bridges with the technique according to the present invention is that e.g. densely sintered high strength alumina can be joined together which results in a dental bridge with high strength, optimal fit and an esthetics which can not be obtained with conventional dental bridges of e.g. metal ceramics.

The size of the particles within the suspension should be large enough such that drying stresses do not lead to catastrophic failure of the bridge unit prior to melting and solidification of the glass material.

The densely sintered bridge parts can be made from such biocompatible oxides as $Al_2O_3$, $TiO_2$, MgO, $ZrO_2$ and $ZrO_2$ with additives of smaller amounts of up to 10 mol % $Y_2O_3$ or MgO (partly or completely stabilized $ZrO_2$). It is important that the ceramic material is sintered to closed porosity, which for an oxide material means at least 98% of theoretical density, but in order to ensure good mechanical strength, the material should preferably have a density over 99% with densities over 99.5% giving the best strength. The following nonlimiting examples are given to illustrate the invention.

Example 1

A suspension of particles with the following composition, by weight, is blended as follows:

| | |
|---|---|
| Acrylic Binder | 1.6 |
| Ammonium PolyAcrylate Dispersant | 1.8 |
| Deionized Water | 12.6 |
| Aluminum Oxide ($d_{50}$ = 3.5 μm) | 84.0 |

Three aluminium oxide parts of density greater than 99.7% were manufactured using methods described in U.S. Pat. No. 5,342,201 and standard uniaxial pressing-techniques. These parts were positioned on a mold such that the suspension could be placed between them to form a particle joint and then allowed to dry. A glass material with the following composition, by mol, was then applied.

| | |
|---|---|
| $SiO_2$ | 32 |
| $B_2O_3$ | 24 |
| $Al_2O_3$ | 18 |
| $La_2O_3$ | 12 |
| $TiO_2$ | 14 |

Figure 3:
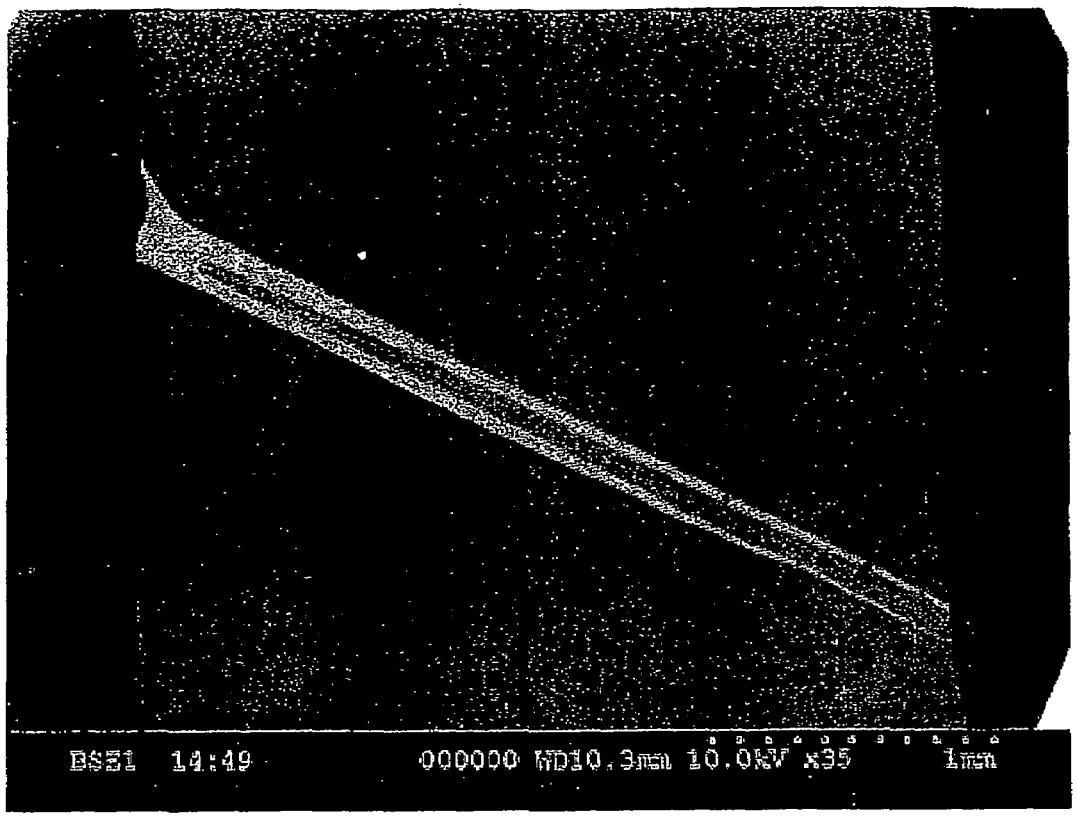
FIG. 3 shows a micrograph of the center of a bridge joint according to the invention.

The unit was then removed from the mold and heated to a temperature of 1200° C. for 1 hour. FIG. 3 shows a micrograph of the center of the bridge-joint. In the micrograph the lighter coloured material is the glass and the darker material is the aluminium oxide. FIG. 3 clearly shows that the densely sintered alumina is completely wetted by the glass material. Hence, the glass material and not the alumina particles bind the two densely sintered pieces of alumina.

The invention claimed is:

1. A method of making artificial dental bridges, comprising:

prior to carrying out any heat treatment applying a premixed suspension comprising aluminum oxide particles to densely sintered high strength ceramic individual bridge parts;

drying the suspension to form a joint of particles between the bridge parts; and applying a suspension of glass material to the joint of particles: and after applying the suspension of particles, drying the suspension of particles and applying the suspension of glass material, then carrying out a one step heat treatment to melt the glass material, thereby forming particle reinforced glass between the bridge parts, wherein the particles are entirely surrounded by glass after the one step heat treatment.

2. The method according to claim 1, wherein the suspension of particles comprises particles, dispersant for the particles, binder for the particles, and a solvent.

3. The method according to claim 1, wherein the suspension of glass comprises $SiO_2$, $B_2O_3$, $Al_2O_3$, $La_2O_3$, and $TiO_2$.

4. The method according to claim 1, wherein the individual bridge parts comprise high strength ceramic material with a relative density greater than 98%.

5. The method according to claim 1, wherein the individual bridge parts comprise one or more of the oxides $Al_2O_3$, $TiO_2$, MgO, $ZrO_2$ or $ZrO_2$ with up to 10 mol % $Y_2O_3$, MgO or CaO.

6. The method according to claim 1, wherein the suspension of glass has a surface energy at a joining temperature lower than a surface energy for the densely sintered individual bridge parts.

7. The method according to claim 1, wherein the suspension of glass material comprises the same metal oxides as the densely sintered high strength ceramic individual bridge parts in an amount less than a degree of saturation of the metal oxides in the suspension of glass material at the joining temperature.

8. The method according to claim 1, wherein the glass material has a coefficient of thermal expansion that is less than or equal to a coefficient of thermal expansion of the densely sintered high strength ceramic individual bridge parts.

9. The method according to claim 1, wherein the glass material comprises $SiO_2$ 32 mol %, $B_2O_3$ 24 mol %, $Al_2O_3$ 18 mol %, and $La_2O_3$ 12 mol %.

10. The method according to claim 1, wherein the particles in the layer of particles are large enough such that drying stresses on removal of solvent from the suspension of glass material do not lead to catastrophic failure of the dental bridge prior to melting and solidification of the glass material.

* * * * *

UNITED STATES PATENT AND TRADEMARK OFFICE
CERTIFICATE OF CORRECTION

| | | |
|---|---|---|
| PATENT NO. | : 7,600,398 B2 | Page 1 of 1 |
| APPLICATION NO. | : 10/500003 | |
| DATED | : October 13, 2009 | |
| INVENTOR(S) | : Salomonson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 203 days.

Signed and Sealed this

Fourteenth Day of December, 2010

David J. Kappos
*Director of the United States Patent and Trademark Office*